United States Patent [19]
Frankel et al.

[11] Patent Number: 4,472,311
[45] Date of Patent: Sep. 18, 1984

[54] METHOD OF PREPARING 1,1,1-AZIDODINITRO COMPOUNDS

[75] Inventors: Milton B. Frankel, Tarzana; Edgar R. Wilson, Simi Valley, both of Calif.

[73] Assignee: Rockwell International Corporation, El Segundo, Calif.

[21] Appl. No.: 400,783

[22] Filed: Jul. 22, 1982

[51] Int. Cl.$^3$ .................... C06B 25/00; C07C 117/00
[52] U.S. Cl. ...................................... 260/349; 149/88
[58] Field of Search ......................................... 260/349

[56] References Cited

U.S. PATENT DOCUMENTS

| | | | |
|---|---|---|---|
| 3,157,683 | 11/1964 | Feuer et al. | 260/349 X |
| 3,317,595 | 5/1967 | Paciorek | 260/349 X |
| 3,883,377 | 5/1975 | Wright | 204/72 X |

OTHER PUBLICATIONS

Fieser, et al., "Reagents for Organic Synthesis", vol. 6, (1977), p. 327; John Wiley & Sons, N.Y.
C.A., 75, (1971), 98106k, Margoretha, et al.
C.A., 82, (1975), 139404w, Henrick, et al.

*Primary Examiner*—Joseph Paul Brust
*Attorney, Agent, or Firm*—H. Fredrick Hamann; Harry B. Field

[57] ABSTRACT

1,1,1-azidodinitro compounds such as 1,1,1-azidodinitroethane are prepared by reacting the corresponding 1,1,1-trinitromethyl compound with lithium azide in the presence of a dipolar aprotic solvent. 1,1,1-azidodinitro compounds are also known as 1-azido-1,1-dinitro compounds.

5 Claims, No Drawings

METHOD OF PREPARING 1,1,1-AZIDODINITRO COMPOUNDS

BACKGROUND OF THE INVENTION

1. Field of the Invention

This invention pertains to the field of propellants and explosives, and more specifically to energetic additives for enhancing performance of these types of pyrotechnics.

2. Description of the Prior Art

Polynitro compounds have proven to be very useful ingredients for all types of propellants and explosive applications. Of particular interest, have been compounds of the 1,1-dinitromethyl class of the following type:

$$RC(NO_2)_2X$$

$$X = NO_2, CH_3, F$$

Such well known compounds would include bis(trinitroethyl) urea (BTNEU), bis(fluorodinitroethyl) formal (FEFO) and bis(dinitropropyl) formal (BDNPF):

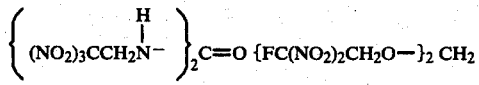

BTNEU      FEFO $$\{CH_3C(NO_2)_2CH_2O-\}_2 CH_2$$

BDNPF

In the continued search for energetic compounds with high oxygen content, the 1,1,1-azidodinitro compounds $RC(NO_2)_2N_3$ appears to be particularly attractive since the azido moiety contributes a positive 80 kcal of energy without detracting from the overall oxygen content.

A very limited amount of work has been done on the chemistry of 1,1,1-azidodinitro compounds. Two compounds of this class were prepared by the electrolysis of a slightly alkaline aqueous solution of a primary gem-dinitroalkane and sodium azide at a smooth platinum electrode. This work is described in U.S. Pat. No. 3,883,377 to C. M. Wright entitled "1-Azido-1,1-Dinitroalkanes".

$$R = CH_3, C_2H_5$$

Both compounds were relatively insensitive to impact $CH_3C(NO_2)_2N_3 = 80$ cm/2 Kg and $CH_3CH_2C(NO_2)_2N_3 = 120$ cm/2 Kg, and possessed thermal stabilities in excess of 100° C. Thus, it appeared that this very energetic class of compounds had reasonable physical properties. However, the electrolysis method of preparing this interesting class of compounds was not very satisfactory since it gave very low yields, required a platinum electrode, and did not lend itself to larger scale production.

SUMMARY OF INVENTION

Accordingly, there is provided by the present invention a chemical method of preparing 1,1,1-azidodinitro compounds wherein the method comprises reacting a 1,1,1-trinitromethyl compound with lithium azide in the presence of a dipolar aprotic solvent.

OBJECTS OF THE INVENTION

Therefore, it is an object of the present invention to provide a chemical method of producing 1,1,1-azidodinitro compounds.

Another object of the present invention is to provide a general chemical method for converting many different classes of known 1,1,1-trinitromethyl compounds to the corresponding 1,1,1-azidodinitro compounds.

A further object of this invention is to demonstrate the conversion of 1,1,1-trinitroethane to 1,1,1-azidodinitroethane, thus showing the practicality of the new process.

Other objects, advantages and novel features of the present invention will become apparent from the following detailed description of the invention when considered in conjunction with the instant disclosure.

DESCRIPTION OF THE PREFERRED EMBODIMENT

A new preparative method has been found for the synthesis of 1,1,1-azidodinitro compounds. The method is based on the treatment of 1,1,1-trinitromethyl compounds with lithium azide in the presence of a dipolar aprotic solvent such as dimethylformamide:

$$RC(NO_2)_3 + LiN_3 \rightarrow RC(NO_2)_2N_3 + LiNO_2$$

In an exploratory experiment, a 28.2% conversion of 1,1,1-trinitroethane to 1,1,1-azidodinitroethane $CH_3C(NO_2)_2N_3$ was achieved. The reaction is undoubtedly unique to lithium azide since trinitromethyl compounds are generally converted to the dinitronate salts on treatment with base:

$$RC(NO_2)_3 + 2MOH \rightarrow RC(NO_2)_2M + MNO_3 + H_2O$$

Other dipolar aprotic solvents such as dimethyl sulfoxide could be used. The reaction temperature can range from about 0° to about 50° C.; however, the preferred range is about 0° to about 5° C. The versatility of the reaction is not limited to 1,1,1-trinitroalkanes but can be extended to other classes of 1,1,1-trinitromethyl compounds, such as esters, formals, and ureas. Thus, it becomes apparent that the key to the present invention is reacting the 1,1,1-trinitromethyl functional group with the lithium azide.

A representative ester would be prepared as follows:

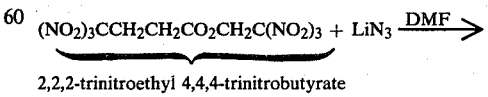

2,2,2-trinitroethyl 4,4,4-trinitrobutyrate

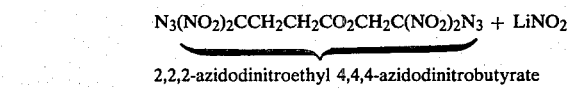

2,2,2-azidodinitroethyl 4,4,4-azidodinitrobutyrate

A representative formal would be prepared as follows:

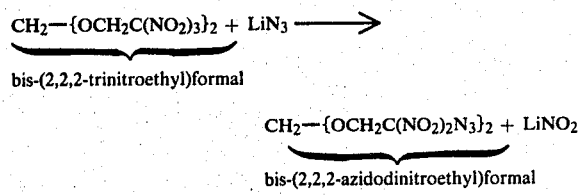

bis-(2,2,2-trinitroethyl)formal
bis-(2,2,2-azidodinitroethyl)formal

A representative urea would be prepared as follows:

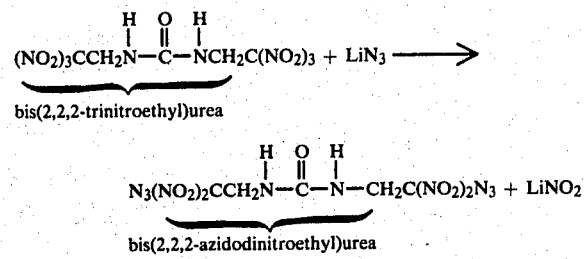

bis(2,2,2-trinitroethyl)urea
bis(2,2,2-azidodinitroethyl)urea

A representative di-(azidodinitro) alkane would be prepared as follows:

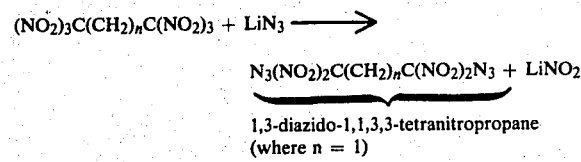

1,3-diazido-1,1,3,3-tetranitropropane
(where n = 1)

It should be noted that in other instances n may be an integer from 0–5 and preferably 1–3.

The general nature of the invention having been set forth, the following example is presented as a specific illustration thereof.

EXAMPLE 10 g (0.2 mole) $LiN_3$ was dissolved in 50-ml dry DMF at room temperature then cooled to 5° C. 16.5 g (0.1 mole) 1,1,1-trinitroethane in 50 ml dry DMF was added dropwise over a period of one hour. Following complete addition the reaction mixture was stirred at 0°–5° C. for 3 hours, then allowed to warm to 20° C. The reaction mixture was then drowned in 500 ml of ice water. The aqueous mixture was extracted twice with 50 ml of methylene chloride. The combined extracts were washed six times with 100 ml deionized water each time to remove DMF. The methylene chloride solution was dried over anhydrous sodium sulfate and then stripped to yield 17.4 g of moist yellow solid. Gas chromatographic analyses shows this mixture to contain 7.8 g of 1,1,1-trinitroethane and 2.4 g of 1,1,1-azidodinitroethane. Yield was 28.2% based on recovered starting material. 1,1,1-azidodinitroethane was identified by retention time on the gas chromatogram compared against an authentic sample. It should be noted that the precise amounts, temperatures, times, solutions, means of addition, drowning procedures, number of washes, extractions and stripping procedures may all be varied to meet specific requirements and specific reactions. These parameters delineated here are merely representative.

Obviously, many modifications and variations of the present invention are possible in light of the above teachings. It is therefore to be understood that, within the scope of the appended claims, the invention may be practiced otherwise than as specifically described.

What is claimed and desired to be secured by Letters Patent of the United States is:

1. A method of preparing an azidodinitro alkane wherein the azido and dinitro groups are located on the same terminal carbon atom and wherein said method comprises the steps of reacting a 1,1,1-trinitroalkane with lithium azide in the presence of a dipolar aprotic solvent and wherein said alkane is a lower alkane having from about 1 to about 5 carbon atoms.

2. The method of claim 1 wherein said alkane has from 1 to 2 carbon atoms.

3. The method of claim 1 wherein said 1,1,1-azidodinitro alkane is a diazido tetranitroalkane.

4. The method of claim 3 wherein said diazido tetranitroalkane has the general formula of $N_3(NO_2)_2C(CH_2)_nC(NO_2)_2N_3$ wherein n is an integer from 0 to about 5.

5. The method of claim 4 wherein n is an integer from 1 to 3.